United States Patent
Hamilton et al.

(10) Patent No.: US 7,164,945 B2
(45) Date of Patent: Jan. 16, 2007

(54) DEFIBRILLATORS

(75) Inventors: Ward Hamilton, Amherst, NH (US); Frederick W. Faller, Burlington, MA (US)

(73) Assignee: ZOLL Medical Corporation, Burlington, MA (US)

( * ) Notice: Subject to any disclaimer, the term of this patent is extended or adjusted under 35 U.S.C. 154(b) by 0 days.

(21) Appl. No.: 09/952,834

(22) Filed: Sep. 14, 2001

(65) Prior Publication Data

US 2003/0055458 A1    Mar. 20, 2003

(51) Int. Cl.
    *A61N 1/18*    (2006.01)
(52) U.S. Cl. ......................................... 607/5
(58) Field of Classification Search .................... 607/4, 607/5, 9, 2; 434/262, 265; 345/594, 700, 345/148, 369, 173
    See application file for complete search history.

(56) References Cited

U.S. PATENT DOCUMENTS

| 4,360,345 A |   | 11/1982 | Hon ............................ 434/262 |
|---|---|---|---|
| 4,583,524 A |   | 4/1986 | Hutchins ..................... 128/1 R |
| 4,588,383 A |   | 5/1986 | Parker et al. ................ 434/265 |
| 4,711,585 A |   | 12/1987 | Fresquez et al. ............ 368/109 |
| 4,797,104 A |   | 1/1989 | Laerdal et al. .............. 434/265 |
| 4,863,385 A | * | 9/1989 | Pierce ......................... 434/265 |
| 5,239,988 A |   | 8/1993 | Swanson et al. .............. 128/28 |
| 5,563,631 A | * | 10/1996 | Masunaga .................... 345/169 |
| 5,593,426 A | * | 1/1997 | Morgan et al. ................. 607/5 |
| 5,797,969 A |   | 8/1998 | Olson et al. |
| 5,913,685 A | * | 6/1999 | Hutchins ..................... 434/265 |
| 6,072,470 A | * | 6/2000 | Ishigaki ....................... 345/158 |
| 6,334,070 B1 | * | 12/2001 | Nova et al. .................... 607/5 |
| 6,356,785 B1 | * | 3/2002 | Snyder et al. ................. 607/5 |
| 6,370,018 B1 | * | 4/2002 | Miller et al. ................ 361/680 |
| 6,405,082 B1 | * | 6/2002 | Borgenicht ..................... 607/5 |
| 6,697,671 B1 | * | 2/2004 | Nova et al. .................... 607/5 |

FOREIGN PATENT DOCUMENTS

WO    WO 00/30712    6/2000

OTHER PUBLICATIONS

"Guidelines 2000 for Cardiopulmonary Resuscitation and Emergency Cardiovascular Care. Part 4: the automated external defibrillator: key link in the chain of survival. The American Heart Association in Collaboration with the International Liaison Committee on Resuscitation." Aug. 22, 2000, Circulation, vol. 102, NR. 8 Suppl., pp. I60-I76.

* cited by examiner

*Primary Examiner*—George Manuel
(74) *Attorney, Agent, or Firm*—Fish & Richardson P.C.

(57) ABSTRACT

Defibrillators are provided that include a graphical user interface to assist a caregiver in administering resuscitation.

15 Claims, 6 Drawing Sheets

DEFIBRILLATORS

TECHNICAL FIELD

This invention relates to defibrillators, and more particularly to automatic external defibrillators (AEDs).

BACKGROUND

Resuscitation treatments for patients suffering from cardiac arrest generally include clearing and opening the patient's airway, providing rescue breathing for the patient, and applying chest compressions to provide blood flow to the victim's heart, brain and other vital organs. If the patient has a shockable heart rhythm, resuscitation also may include defibrillation therapy.

There are many different kinds of abnormal heart rhythms, some of which can be treated by defibrillation therapy ("shockable rhythms") and some which cannot (non-shockable rhythms"). For example, most ECG rhythms that produce significant cardiac output are considered non-shockable (examples include normal sinus rhythms, certain bradycardias, and sinus tachycardias). There are also several abnormal ECG rhythms that do not result in significant cardiac output but are still considered non-shockable, since defibrillation treatment is usually ineffective under these conditions. Examples of these non-shockable rhythms include asystole, electromechanical disassociation and other pulseless electrical activity. Although a patient cannot remain alive with these non-viable, non-shockable rhythms, applying shocks will not help convert the rhythm. The primary examples of shockable rhythms, for which the caregiver should perform defibrillation, include ventricular fibrillation, ventricular tachycardia, and ventricular flutter.

After using a defibrillator to apply one or more shocks to a patient who has a shockable ECG rhythm, the patient may nevertheless remain unconscious, in a shockable or non-shockable, perfusing or non-perfusing rhythm. If a non-perfusing rhythm is present, the caregiver may then resort to performing CPR for a period of time in order to provide continuing blood flow and oxygen to the patient's heart, brain and other vital organs. If a shockable rhythm continues to exist or develops during the delivery of CPR, further defibrillation attempts may be undertaken following this period of cardiopulmonary resuscitation. As long as the patient remains unconscious and without effective circulation, the caregiver can alternate between use of the defibrillator (for analyzing the electrical rhythm and possibly applying a shock) and performing cardiopulmonary resuscitation (CPR). CPR generally involves a repeating pattern of five or fifteen chest compressions followed by a pause during which two rescue breaths are given.

Defibrillation can be performed using an AED. The American Heart Association, European Resuscitation Council, and other similar agencies provide protocols for the treatment of victims of cardiac arrest that include the use of AEDs. These protocols define a sequence of steps to be followed in accessing the victim's condition and determining the appropriate treatments to be delivered during resuscitation. Caregivers who may be required to use an AED are trained to follow these protocols.

Most automatic external defibrillators are actually semi-automatic external defibrillators (SAEDs), which require the caregiver to press a start or analyze button, after which the defibrillator analyzes the patient's ECG rhythm and advises the caregiver to provide a shock to the patient if the electrical rhythm is shockable. The caregiver is then responsible for pressing a control button to deliver the shock. Following shock delivery, the SAED may reanalyze the patient's ECG rhythm, automatically or manually, and advise additional shocks or instruct the caregiver to check the patient for signs of circulation (indicating that the defibrillation treatment was successful or that the rhythm is non-shockable) and to begin CPR if circulation has not been restored by the defibrillation attempts. Fully automatic external defibrillators, on the other hand, do not wait for user intervention before applying defibrillation shocks. As used below, automatic external defibrillators (AED) include semi-automatic external defibrillators (SAED).

Both types of defibrillators typically provide an auditory "stand clear" warning before beginning ECG analysis and/or the application of each shock. The caregiver is then expected to stand clear of the patient (i.e. stop any physical contact with the patient) and may be required to press a button to deliver the shock. The controls for automatic external defibrillators are typically located on a resuscitation control box.

AEDs are typically used by trained medical or paramedic caregivers, such as physicians, nurses, emergency medical technicians, fire department personnel, and police officers. The ready availability of on-site AEDs and caregivers trained to operate them is important because a patient's chances of survival from cardiac arrest decrease by approximately 10% for each minute of delay between occurrence of the arrest and the delivery of defibrillation therapy.

Trained lay caregivers are a new group of AED operators. For example, spouses of heart attack victims may become trained as lay caregivers. Lay caregivers rarely have opportunities to defibrillate or deliver CPR, and thus they can be easily intimidated by an AED during a medical emergency. Consequently, such lay providers may be reluctant to purchase or use AEDs when needed, or might tend to wait for an ambulance to arrive rather than use an available AED, out of concern that the lay provider might do something wrong.

Some trained medical providers, e.g., specialists such as obstetricians, dermatologists, and family care practitioners, also rarely have the opportunity to perform CPR and/or defibrillate, and thus may be uneasy about doing so. Concerns about competence are exacerbated if training is infrequent, leading the caregiver to worry that he or she may not be able to remember all of the recommended resuscitation protocol steps and/or their correct sequence.

Similarly, both medical and lay caregivers may be hesitant to provide CPR and rescue breathing, or may be unsure when these steps should be performed, particularly if their training is infrequent and they rarely have the opportunity to use it.

SUMMARY

The invention provides a graphical user interface for use with an AED. The graphical user interface includes a set of graphics that clearly indicate the steps that should be performed by a trained caregiver administering resuscitation to a victim of cardiac arrest. The graphics, which may be accompanied by audio prompts and/or other visually displayed messages, provide visual reminders that will assist and encourage trained caregivers who might not otherwise feel competent to perform cardiac resuscitation including the use of an AED. In the case of caregivers who are confident of their training and skills, the visual prompts may aid the caregiver in more quickly and efficiently performing the required steps in the resuscitation sequence.

In one aspect, the invention features a defibrillator including: (a) electrodes configured to be attached to a patient, to acquire data indicative of the patient's heart rhythm and to deliver a defibrillating shock if appropriate; (b) a defibrillator control box connected to the electrodes; and (c) on a portion of the defibrillator control box, a series of graphics configured to prompt a caregiver to perform a sequence of steps appropriate for treating a victim of suspected cardiac arrest.

Some implementations of the invention may include one or more of the following features. The graphics include one or more of the following pictures: a picture configured to prompt the caregiver to check the patient for responsiveness, a picture configured to prompt the caregiver to call for emergency assistance, a picture configured to prompt the caregiver to open the patient's airway, a picture configured to prompt the caregiver to check the patient's pulse, a picture configured to prompt the caregiver to attach the electrodes to the patient, a picture configured to prompt the caregiver to stand clear of the patient, a picture configured to prompt the caregiver to press a treatment button to cause the defibrillator to administer a defibrillating shock, and a picture configured to prompt the caregiver to perform CPR. Preferably, the pictures illustrate how the steps are to be performed, e.g., how to open the patient's airway, where the electrodes should be attached, and how to perform chest compressions and rescue breathing.

Generally, if the defibrillator is an SAED, the defibrillator will further include a treatment button configured to be pressed by the caregiver to cause the defibrillator to administer a defibrillating shock. The location of the treatment button may be indicated by a graphic, e.g., a heart symbol.

In some implementations, the defibrillator further includes a light source associated with each of the graphics in the series. The defibrillator may include electronics configured to sequentially illuminate the light sources. The sequential illumination may be controlled by electronics configured to measure the time elapsed from the time at which the caregiver turned the power on to activate the defibrillator, at least some of the light sources being sequentially illuminated based on the elapsed time. Alternatively, or in addition, sequential illumination may be controlled by electronics configured to be preprogrammed with times for the illumination of the light sources, at least some of the times being based on the time elapsed from (a) the time at which the previous light source in the sequence was first illuminated or (b) the time when a shock was delivered to the patient. The sequential illumination of some of the light sources may be controlled by electronics configured to acquire data from the electrodes, at least some of the light sources being sequentially illuminated based on the data acquired from the electrodes. The light sources may be illuminated based on an algorithm, e.g., an algorithm that takes into account one or more of the following items of data: (a) the time elapsed from the time at which the previous light source in the sequence was first illuminated, and/or (b) the time elapsed from the last time a shock was delivered to the patient, and/or (c) the results of ECG analysis.

In some implementations, the defibrillator also includes electronics configured to provide audio prompts to the caregiver. The audio prompts may be timed in any of the manners described above with regard to the sequential illumination of the light sources. Generally, the audio prompts are associated with the series of graphics and are given sequentially to guide the caregiver through the sequence of steps, and the audio prompts are also associated with the sequential illumination of the light sources.

At least some of the graphics may be provided on a cover portion of the defibrillator control box. These graphics may be provided on the inside and/or outside of the cover. If the graphics are provided on the outside of the cover, they may include a picture indicating that the cover should be removed from the defibrillator. The cover may include a space provided for local emergency information, e.g., a window behind which a card bearing local emergency information can be placed.

The graphics may be provided in any desired manner, for example, in the form of backlit, translucent images, as an electronic display, or in the form of a decal.

In another aspect, the invention features a system for prompting a caregiver in a resuscitation sequence for a patient who may be suffering from cardiac arrest. The system includes: (a) electrodes constructed to acquire data, indicative of the heart rhythm of the patient and indicative of whether the electrodes are properly placed on the patient, (b) a defibrillator control box, connected to the electrodes, constructed to analyze data received from the electrodes and to measure the time elapsed since the defibrillator control box was activated by the caregiver and/or since the last shock was delivered to the patient; and (c) a user interface constructed to display information concerning the appropriate step of the resuscitation sequence to be performed by the caregiver at a particular time, based on the data received from the electrodes and the elapsed time.

In yet another aspect, the invention features a defibrillator including: (a) electrodes configured to be attached to a patient, to acquire data indicative of the patient's heart rhythm and to deliver a defibrillating shock if appropriate; (b) a defibrillator control box connected to the electrodes; (c) a treatment button configured to be pressed by a caregiver to deliver a defibrillating shock, the location of the treatment button being indicated by a heart symbol; and (e) electronics configured to cause the heart symbol to be temporarily illuminated if a shock is advised based on ECG analysis performed by the defibrillator control box.

In preferred implementations, the graphical interface illustrates the entire sequence of resuscitation activities that are recommended by the American Heart Association. As a result, the graphical interface helps both experienced and novice users to get through the early steps of patient care that are included in the AHA's resuscitation protocols.

Moreover, because "a picture is worth a thousand words", the graphical interface reminds the caregiver of how the steps in the AHA's resuscitation protocols should be performed. For example, rather than simply prompting the caregiver to "check airway", the graphical interface reminds the caregiver that this means that the caregiver should perform the head-tilt chin lift maneuver. To provide the same information using audio or textual prompts alone could inundate the care giver with detailed information that could confuse the caregiver. The graphical interface allows the caregiver to use his or her visual senses in order to remember what to do at each step during the rescue. The pictures may, also, be helpful when the rescue is being performed in a noisy environment when voice prompts may be hard to hear.

Other features and advantages of the invention will be apparent from the description and drawings, and from the claims.

DESCRIPTION OF DRAWINGS

FIG. 1 is a perspective view of an AED with its cover on.

DETAILED DESCRIPTION

Figure 1:
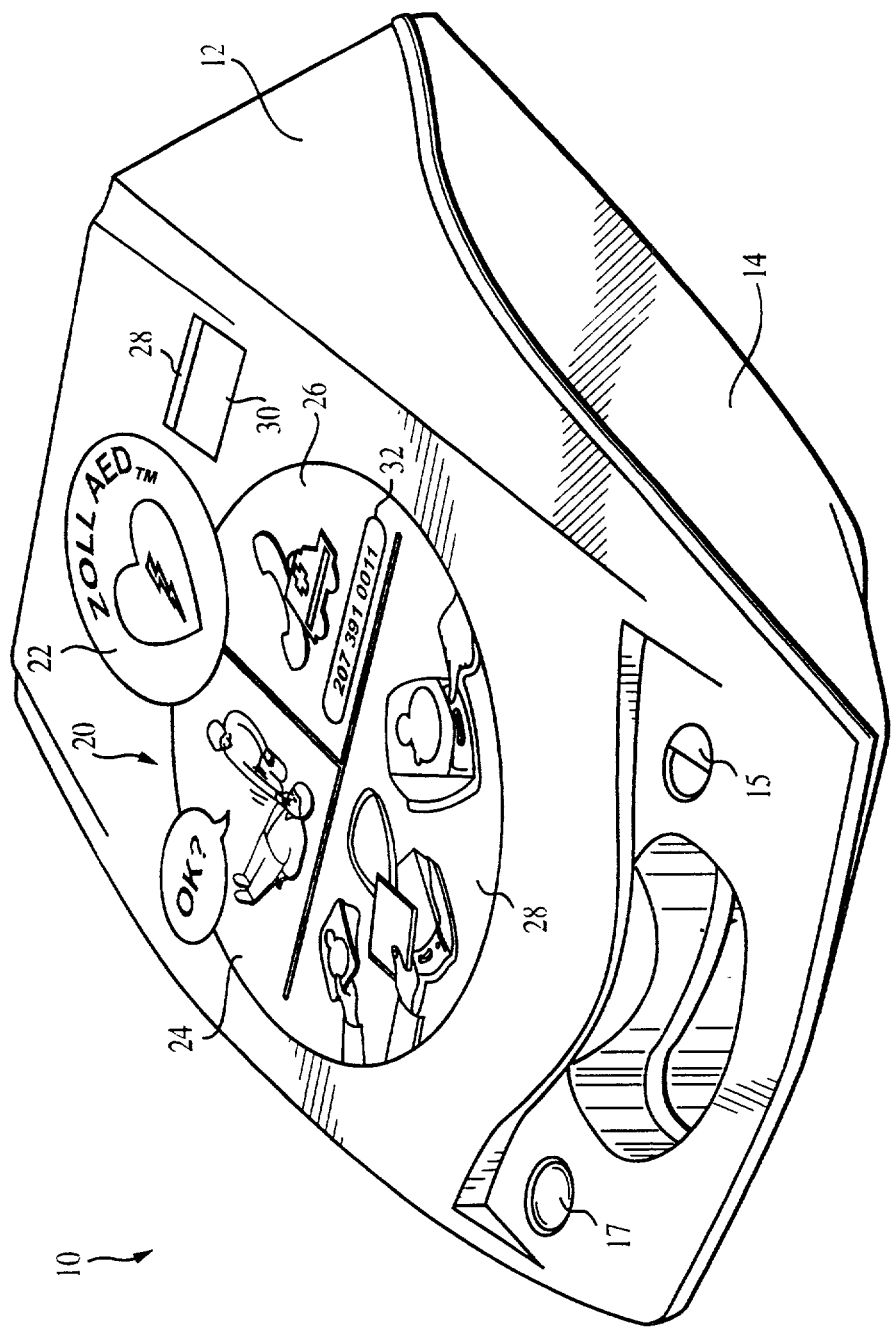

Referring to FIG. 1, an automated external defibrillator 10 includes a removable cover 12 and a control box 14. The defibrillator 10 is shown with cover 12 removed in FIG. 2. An electrode assembly 16 (or a pair of separate electrodes) is connected to the control box 14 by a cable 18. Electrode assembly 16 is stored under cover 12 when the defibrillator is not in use.

Control box 14 includes a power button 15 and a status indicator 17. Status indicator 17 indicates to the caregiver whether the defibrillator is ready to use.

Figure 3:
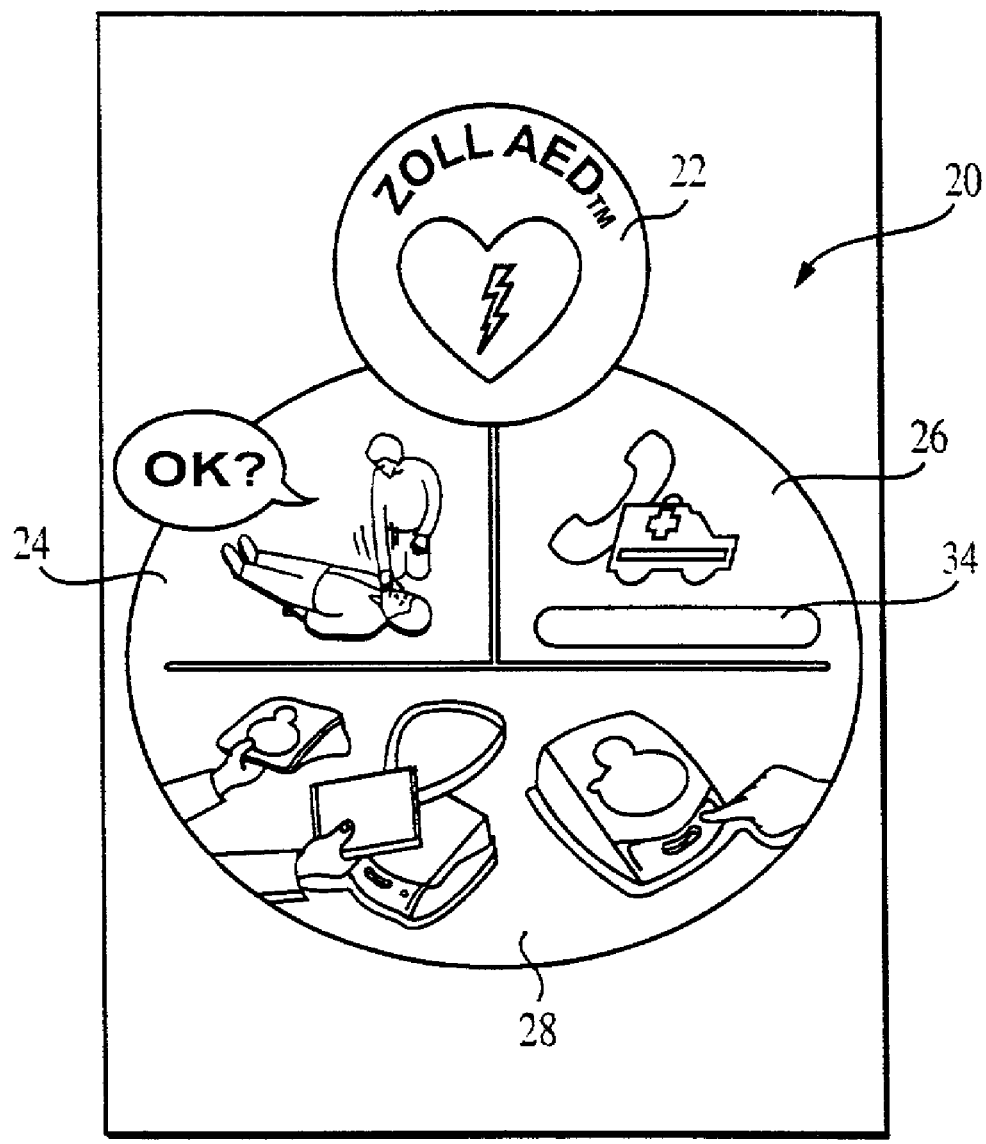
FIG. 3 is a plan view of the graphical interface decal used on the cover of the AED of FIG. 1.

The cover 12 includes a cover decal 20 (FIGS. 1 and 3) including a logo 22 and a series of graphics 24, 26 and 28. Logo 22 may provide information concerning the manufacturer of the device and that the device is a defibrillator (e.g., "Zoll AED", as shown in FIG. 3, indicating that the device is a Semi-automatic External Defibrillator available from Zoll Medical). Graphics 24, 26 and 28 lead the caregiver through the initial stages of a cardiac resuscitation sequence as outlined in the AHA's AED treatment algorithm for Emergency Cardiac Care pending arrival of emergency medical personnel. (See "Guidelines 2000 for Cardiopulmonary Resuscitation and Emergency Cardiovascular Care. Supplement to Circulation," Volume 102, Number 8, Aug. 22, 2000, pp. 1–67.) Thus, graphic 24, showing the caregiver and patient, indicates that the caregiver should first check the patient for responsiveness, e.g., by shaking the patient gently and asking if the patient is okay. Next, graphic 26, showing a telephone and an emergency vehicle, indicates that the caregiver should call for emergency assistance prior to administering resuscitation. Finally, graphic 28 indicates that after these steps have been performed the caregiver should remove the lid 12 of the defibrillator, remove the electrode assembly 16 stored under the lid, and turn the power on by depressing button 15. The graphics are arranged in clockwise order, with the first step in the upper left, since this is the order most caregivers would intuitively follow. However, in this case the order in which the caregiver performs the steps is not critical, and thus for simplicity no other indication of the order of steps is provided.

The cover may also include a slot 28 (FIG. 1), through which a card bearing local emergency information can be inserted and a transparent window 30, communicating with slot 28, through which the card can be viewed. Alternatively, or in addition, this information can be displayed on a decal to be applied to the cover by a user, e.g., phone number decal 32 (FIG. 1) applied to area 34 (FIG. 3) of cover decal 20. These features allow the emergency information to be customized for a particular location and to be easily updated if changes occur.

Figure 2:
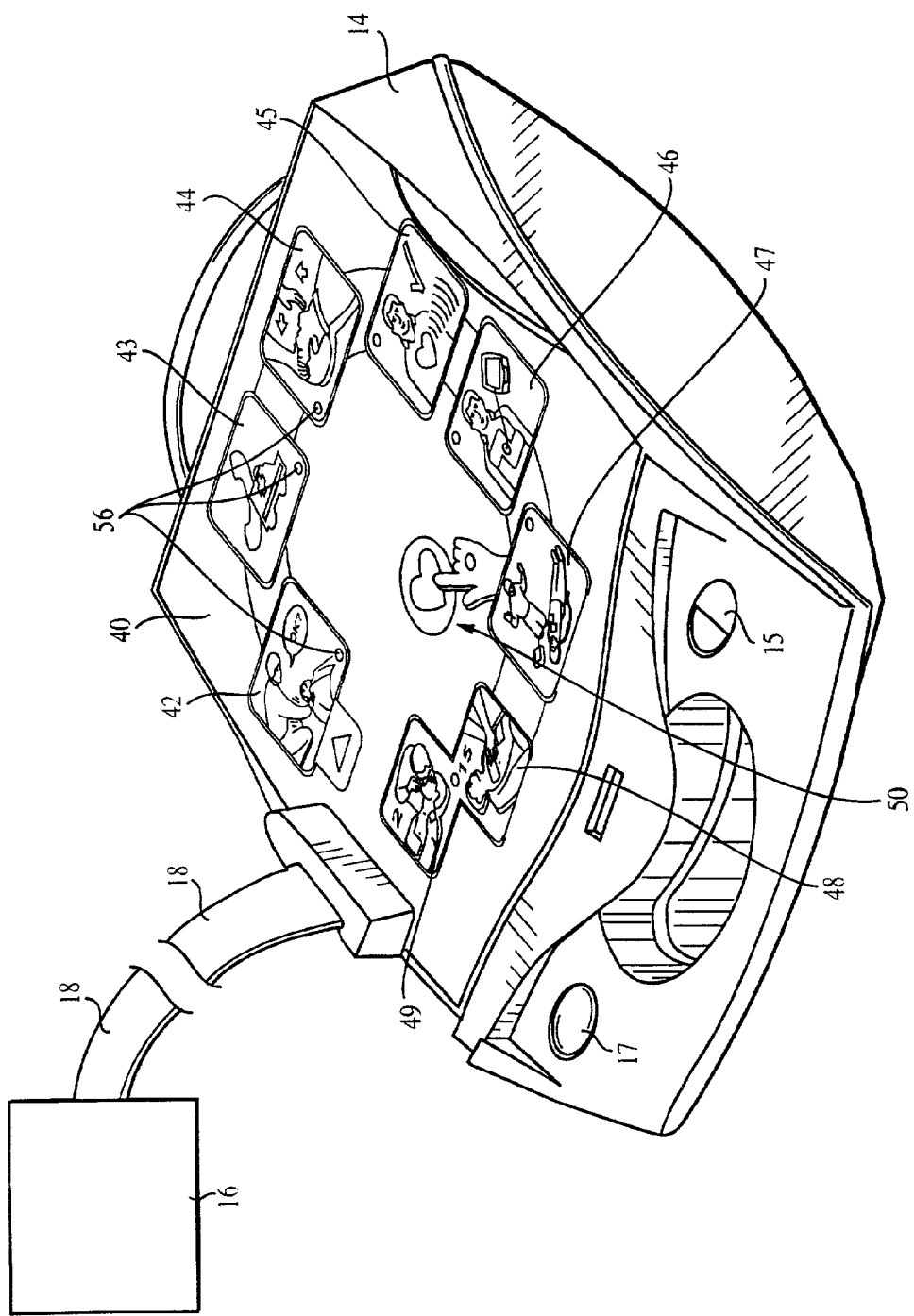
FIG. 2 is a perspective view of the AED of FIG. 1 with the cover removed.
Figure 4:
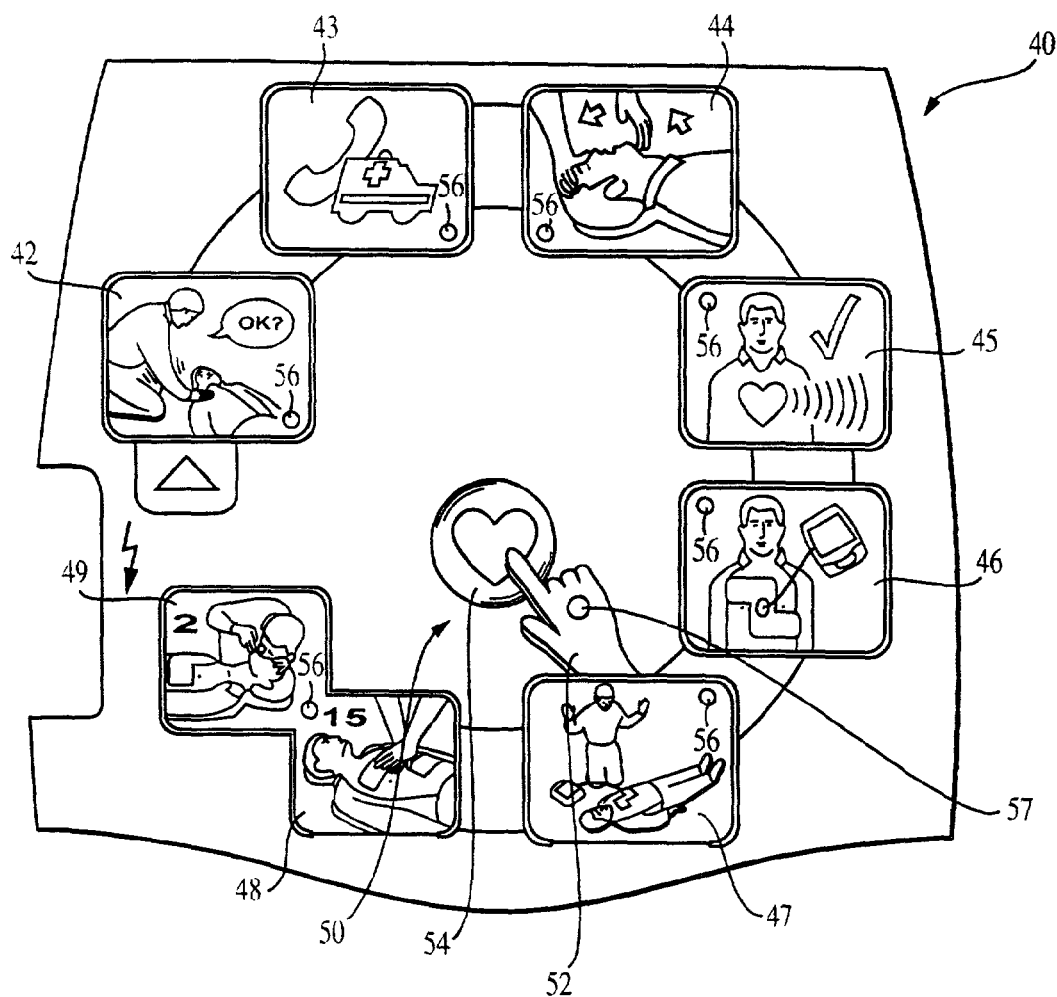
FIG. 4 is a plan view of the graphical interface decal used on the control box of the AED of FIG. 1, as shown in FIG. 2.

The control box includes a control box decal 40, shown in FIGS. 2 and 4. Decal 40, like decal 20, includes a series of graphics 42–49 (FIG. 4). In this case, the graphics are configured to lead the caregiver through the entire resuscitation sequence, as will be explained below with reference to FIG. 5. Decal 40 also includes a center graphic 50, which includes representations of a hand 52 and a heart 54 (FIG. 4). Center graphic 50 overlies a treatment button which, when depressed, causes the defibrillator to deliver a defibrillating shock to the electrode assembly 16.

Each of the graphics on control box decal 40 is accompanied by a light source that can be temporarily illuminated to indicate that the illuminated step should be performed at that particular time. These light sources guide the caregiver, step-by-step, through the resuscitation sequence, indicating which graphic should be viewed at each point in time during resuscitation.

The light source for each of the graphics 42–49 is preferably an adjacent LED (LEDs 56, FIG. 2). The heart 54 may be translucent and backlit by a light source in the control box (not shown). Alternatively, the heart 54 may include an adjacent LED (not shown) and/or the hand 52 may include an LED 57 as shown.

LEDs 56 and 57 are mounted on the control box and are visible through openings in the decal 40. When the heart 54 and/or hand 52 is illuminated, this indicates to the caregiver that the underlying treatment button should be depressed to administer a defibrillating shock, as will be discussed in further detail below.

Programmable electronics within the control box 14 are used to determine when each of the light sources should be illuminated.

The illumination and subsequent turning off of the LEDs adjacent to graphics 42–45 is based on the amount of time that has elapsed since the caregiver turned the power on by depressing button 15. The elapsed time is measured by the programmable electronics and used to illuminate each of the LEDs associated with graphics 42–45 in turn. A time lapse of about 2 to 15 seconds is allowed between each illumination, to allow the caregiver an appropriate amount of time to perform each step. These time intervals vary from a few seconds for graphic 42 (check responsiveness) to 10 or more seconds for graphic 44 (open airway, check for breathing).

The illumination of the LED adjacent to graphic 46 is based on the elapsed time, while the subsequent turning off of this LED is based on whether the impedance measured by the programmable electronics indicates that the electrodes of electrode assembly 16 have been correctly positioned on the patient. This LED remains lit until the correct impedance between the electrodes is detected, e.g., an impedance of less than 300 ohms.

The illumination and turning off of the LEDs adjacent to graphics 47–49, and of the light behind heart 54, is based on ECG data that is acquired by electrode assembly 16 and analyzed by the programmable electronics, as will be discussed below with reference to FIG. 5.

The programmable electronics may also provide audio prompts, timed to coincide with the illumination of the light sources, as will also be discussed below with reference to FIG. 5.

Figure 5:
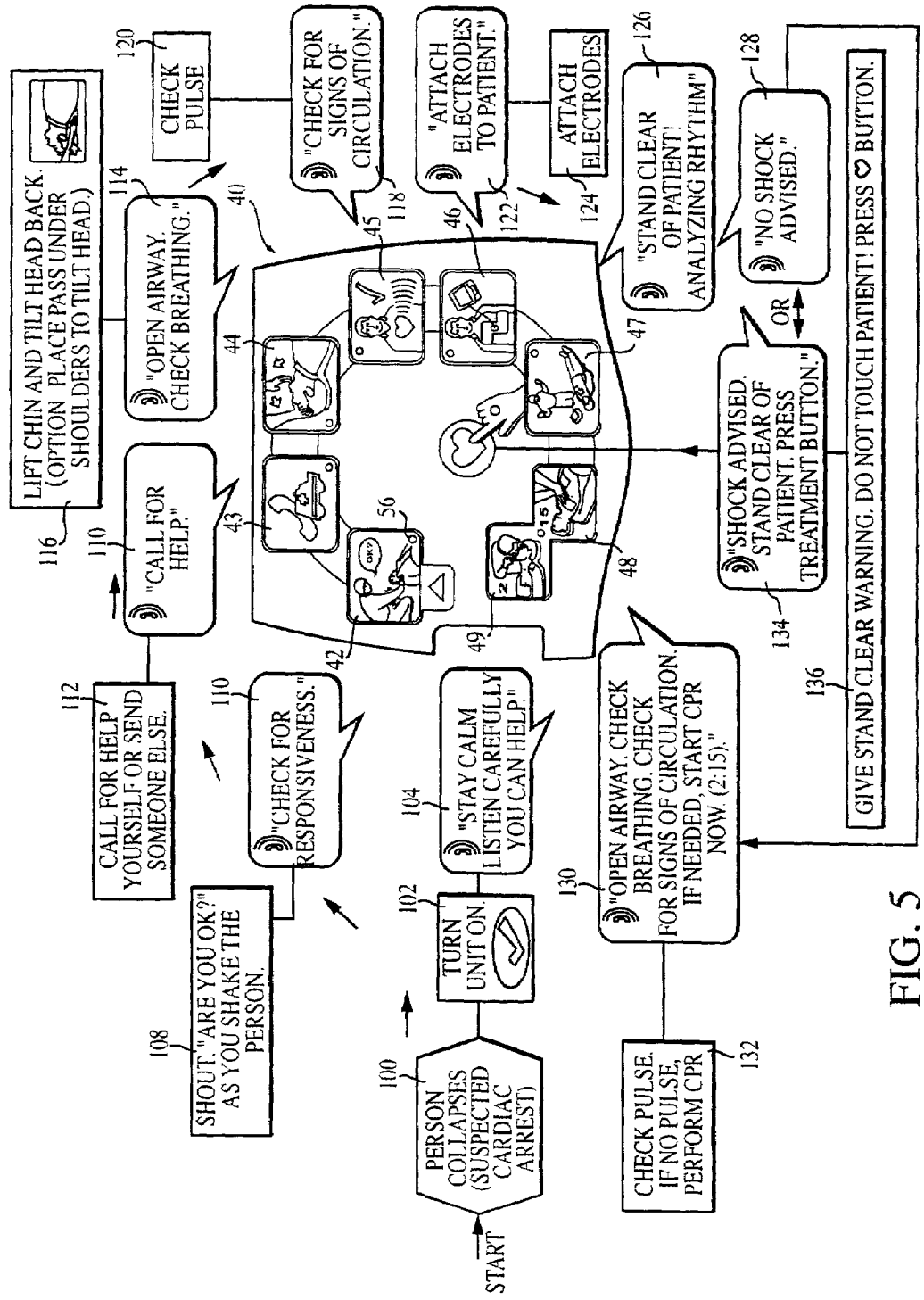
FIG. 5 is a flow chart indicating audio prompts provided during use of the AED of FIG. 1 and steps to be performed by the caregiver in response to the graphical and audio prompts.
Figure 6:
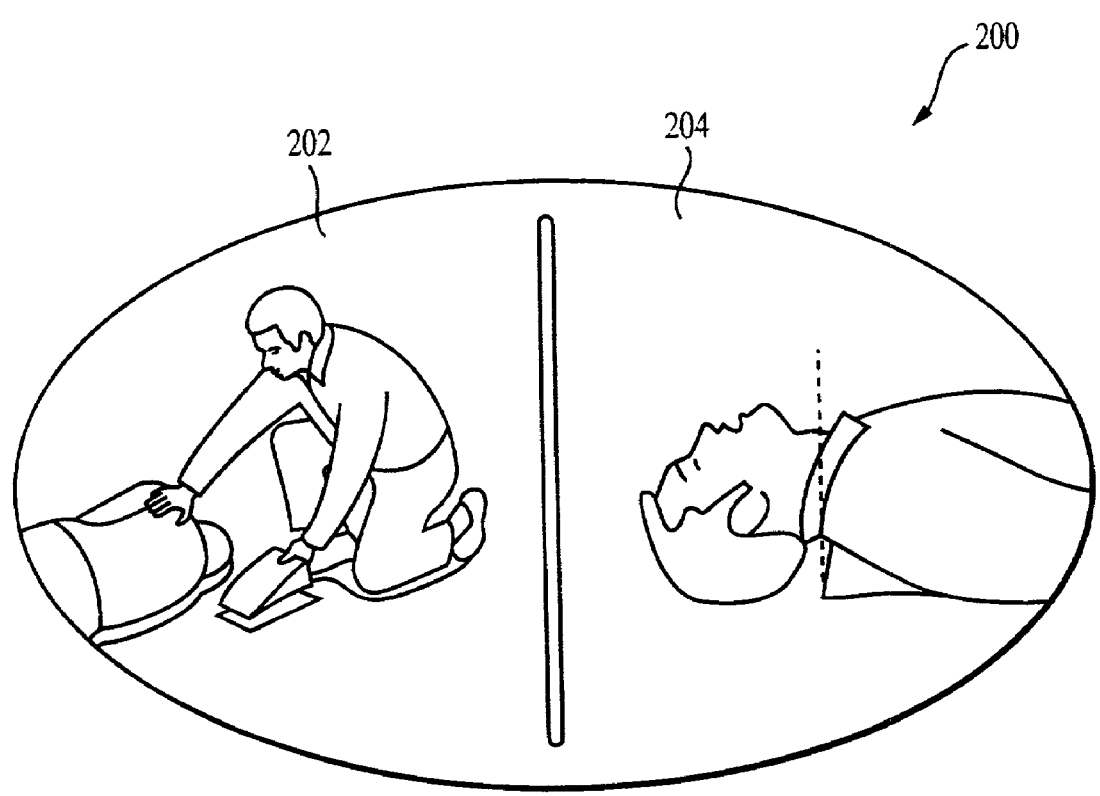
FIG. 6 is a plan view of a graphical interface decal used on the underside of the cover of the AED of FIG. 1.

FIG. 5 illustrates, in flow chart form, the use of the graphics on decal 40, and accompanying visual and audio prompts, by a caregiver performing resuscitation. The text in boxes indicates steps performed by the caregiver. The text in caption balloons, with ear symbols, indicates audio prompts generated by the defibrillator.

Thus, when a person collapses and a caregiver suspects that the person is in cardiac arrest (100), the caregiver first gets the defibrillator and turns the power on (102). If the unit passes its internal self tests, and is ready for use, this will be indicated by indicator 17, as discussed above. Next, the defibrillator prompts the caregiver with an introductory audio message, e.g., "Stay calm. Listen carefully." (Audio prompt 104.)

Shortly thereafter, the defibrillator will prompt the caregiver with an audio message indicating that the caregiver should check the patient for responsiveness (audio prompt 106). Simultaneously, the LED adjacent graphic 42 will light up, directing the caregiver to look at this graphic. Graphic 42 will indicate to the caregiver that she should shout "are you OK?" and shake the person (step 108) in order to determine whether the patient is unconscious or not.

After a suitable period of time has elapsed (e.g., 2 seconds), if the caregiver has not turned the defibrillator power off (as would occur if the patient were responsive), the defibrillator will give an audio prompt indicating that the caregiver should call for help (audio prompt 110). Simultaneously, the LED adjacent graphic 42 will turn off and the LED adjacent graphic 43 will light up, directing the caregiver's attention to graphic 43. Graphic 43 will remind the caregiver to call emergency personnel (step 112), if the caregiver has not already done so.

After a suitable interval has been allowed for the caregiver to perform step 112 (e.g., 2 seconds since audio prompt 110) the defibrillator will give an audio prompt indicating that the caregiver should open the patient's airway and check whether the patient is breathing (audio prompt 114). The LED adjacent graphic 43 will turn off, and the LED adjacent graphic 44 will light up, directing the caregiver's attention to graphic 44, which shows the proper procedure for opening a patient's airway. This will lead the caregiver to lift the patient's chin and tilt the patient's head back (step 116). The caregiver may also position an airway support device under the patient's neck and shoulders, if desired, as discussed below with reference to FIG. 7. The caregiver will then check to determine whether the patient is breathing.

After a suitable interval (e.g., 15 seconds since audio prompt 114), the defibrillator will give an audio prompt indicating that the caregiver should check for signs of circulation (audio prompt 118), the LED adjacent graphic 44 will turn off, and the LED adjacent graphic 45 will light up. Graphic 45 will indicate to the caregiver that the patient should be checked for a pulse or other signs of circulation as recommended by the AHA for lay rescuers (step 120).

After a suitable interval (e.g., 5 to 7 seconds since audio prompt 118), the defibrillator will give an audio prompt indicating that the caregiver should attach electrode assembly 16 to the patient (audio prompt 122), the LED adjacent graphic 45 will turn off, and the LED adjacent graphic 46 will light up. Graphic 46 will indicate to the caregiver how the electrode assembly 16 should be positioned on the patient's chest (step 124). The defibrillator will periodically repeat audio prompt 122 every 15 seconds until the electrodes are properly connected to the patient.

When the impedance data received from the electrode assembly indicates that the electrodes are properly positioned and in contact with the patient's skin, the defibrillator will stop audio prompt 122 and turn off the LED adjacent graphic 46. At this point, the LED adjacent graphic 47 will light up, and the defibrillator will give an audio prompt indicating that the patient's heart rhythm is being analyzed by the defibrillator and the caregiver should stand clear (audio prompt 126). While this LED is lit, the defibrillator will acquire ECG data from the electrode assembly, and analyze the data to determine whether the patient's heart rhythm is shockable. This analysis is conventionally performed by AEDs.

If the defibrillator determines that the patient's heart rhythm is not shockable, the defibrillator will give an audio prompt such as "No shock advised" (audio prompt 128). The LEDs next to graphics 48 and 49 will then light up, and the defibrillator will give an audio prompt indicating that the caregiver should again open the patient's airway, check for breathing and a pulse, and, if no pulse is detected by the caregiver, then commence giving CPR (audio prompt 130, step 132). Graphics 48 and 49 will remind the caregiver of the appropriate steps to perform when giving CPR.

Alternatively, if the defibrillator determines that the patient's heart rhythm is shockable, the defibrillator will give an audio prompt such as "Shock advised. Stand clear of patient. Press treatment button." (Audio prompt 134.) At the same time, the heart 54 and/or hand 52 will light up, indicating to the caregiver the location of the treatment button. At this point, the caregiver will stand clear (and warn others, if present, to stand clear) and will press the heart 54, depressing the treatment button and administering a defibrillating shock (or a series of shocks, as determined by the defibrillator electronics) to the patient (step 136).

After step 136 has been performed, the defibrillator will automatically reanalyze the patient's heart rhythm, during which audio prompt 126 will again be given and graphic 47 will again be illuminated. The analyze and shock sequence described above will be repeated up to three times if a shockable rhythm is repeatedly detected or until the defibrillator is turned off or the electrodes are removed. After the third shock has been delivered, the device will illuminate LEDs 48 and 49 and issue the audio prompts 130/132. The device will keep LEDs 48 and 49 illuminated for a period of approximately one minute indicating that if CPR is performed, it should be continued for the entire minute. "Continue CPR" audio prompts may be repeated every 15–20 seconds during this period to instruct the user to continue performing chest compressions and rescue breathing.

After approximately one minute has elapsed, the device will extinguish LEDs 48 and 49 and illuminate LED 47. Audio prompt 126 (stand clear, analyzing rhythm) will also be issued and a new sequence of up to three ECG analyses/shocks will begin.

If the caregiver detects circulation during step 132, the caregiver may turn off the defibrillator and/or remove the electrodes. Alternatively, the caregiver may not perform further CPR, but nonetheless allow the device to reanalyze the ECG after each one minute CPR period in order to provide repeated periodic monitoring to ensure the patient continues to have a non-shockable rhythm.

Thus, in the continuing presence of a shockable rhythm, the sequence of three ECG analyses and three shocks, followed by one minute of CPR, will continue indefinitely. If, instead, a non-shockable rhythm is or becomes present, the sequence will be analyze/no shock advised, one minute of CPR, analyze/no shock advised, one minute of CPR, etc. When a shock is effective in converting the patient's heart rhythm to a heart rhythm that does not require further defibrillating treatment, the sequence will be: analyze/shock advised, shock (saves patient), analyze/no shock advised, one minute CPR period (if pulse is detected then caregiver will not do CPR during this period), analyze/no shock advised, one minute CPR period, etc., continuing until the caregiver turns the defibrillator (e.g., if the caregiver detects a pulse) or the electrodes are removed.

If electrode contact is lost at any time (as determined by the impedance data received from the electrode assembly), this will result in an appropriate audio prompt, such as "check electrodes" and illumination of the LED adjacent graphic 46.

Other embodiments are within the scope of the following claims.

For example, the graphics on the center decal can be accompanied by any desired light source. For instance, if desired, all of the graphics can be translucent, and can be backlit. Alternatively, the graphics can be provided in the form of electronic display images, rather than on a decal.

While it is generally preferred that audio prompts and visual (light source) prompts be used, these features may be omitted if desired.

Moreover, while the electrodes have been illustrated in the form of an integral electrode assembly, separate electrodes may be used.

In preferred implementations, generally all of the graphically illustrated steps are shown at the same time, e.g., as illustrated by the decal described above. This arrangement allows the caregiver to see the steps that will be performed next and thus anticipate the next step and begin it early if possible. However, alternatively, the graphics can be displayed one at a time, e.g., by using a screen that displays one graphic at a time or backlit graphics that are unreadable when not back lit. This arrangement may in some cases avoid overwhelming novice or lay rescuers, because it does not present the caregiver with too much information all at the same time.

If desired, each graphic could have an associated button which, when pressed, causes more detailed audio prompts related to that graphic to be output by the defibrillator.

The cover 12 of the AED may include a decal on its underside, e.g., decal 200 shown in FIG. 7. Decal 200 illustrates the use of the cover as a passive airway support device, to keep the patient's airway open during resuscitation. Graphic 202 prompts the caregiver to roll the patient over and place cover 12 under the patient's shoulders, and graphic 204 illustrates the proper positioning of the cover 12 under the patient to ensure an open airway.

While such a graphic is not included in the decal shown in FIG. 4, the decal 40 may include a graphic that would prompt the user to check to see if the patient is breathing. Such a graphic may include, e.g., a picture of the caregiver with his ear next to the patient's mouth. The graphic may also include lines indicating flow of air from the patient's mouth.

"Illuminated", "light up", and similar terms are used herein to refer to both a steady light and a blinking light. A blinking light may be used, if desired, to more clearly draw the user's attention to the associated graphic.

What is claimed is:

1. A defibrillator comprising:
    electrodes configured to be attached to a patient, to acquire data indicative of the patient's heart rhythm and to deliver a defibrillating shock if appropriate;
    a defibrillator control box connected to the electrodes;
    on a portion of the defibrillator control box, a series of graphics configured to prompt a caregiver to perform a sequence of steps appropriate for treating a victim of suspected cardiac arrest,
    electronics configured to acquire data from the electrodes, and electronics configured to illuminate at least some of the light sources in a sequence based at least in part on the data acquired from the electrodes.

2. The defibrillator of claim 1 wherein the defibrillator control box comprises electronics configured to provide audio prompts to the caregiver, wherein the audio prompts are associated with the series of graphics and are given sequentially to guide the caregiver through the sequence of steps, and wherein at least some of the audio prompts are timed to occur based on the data acquired from the electrodes.

3. The defibrillator of claim 2 further comprising electronics configured so that at least some of the audio prompts are timed to occur based on the time elapsed from the time at which a shock was last delivered to the patient.

4. A defibrillator comprising:
    electrodes configured to be attached to a patient, to acquire data indicative of the patient's heart rhythm and to deliver a defibrillating shock if appropriate;
    a defibrillator control box connected to the electrodes; and
    on a portion of the defibrillator control box, a series of graphics configured to prompt a caregiver to perform a sequence of steps appropriate for treating a victim of suspected cardiac arrest,
    further comprising buttons, associated with at least some of the graphics, and electronics which, when the buttons are pressed, provide audio prompts related to the associated graphic to be output by the defibrillator.

5. A system for prompting a caregiver in a resuscitation sequence for a patient who may be suffering from cardiac arrest, comprising
    electrodes constructed to acquire data, indicative of the heart rhythm of the patient and indicative of whether the electrodes are properly placed on the patient,
    a defibrillator control box capable of being activated and delivering a shock to the patient through the electrodes, the control box being connected to the electrodes, and being constructed to analyze data received from the electrodes and to measure the time elapsed since the defibrillator control box was activated by the caregiver or since the last shock was delivered to the patient; and
    a user interface constructed to display information concerning the appropriate step of the resuscitation sequence to be performed by the caregiver at a particular time, based on the data received from the electrodes and the elapsed time.

6. The defibrillator of claim 1, 4, or 5
    wherein the graphics include a picture that includes at least a portion of a user's hand depressing a treatment button to prompt the caregiver to press the treatment button to cause the defibrillator to administer a defibrillating shock.

7. The defibrillator of claim 6 wherein the picture includes a heart symbol indicating the location of the treatment button.

8. The defibrillator of claim 7 wherein the picture includes at least a portion of a hand and finger on or adjacent to the heart symbol indicating that the symbol is intended to be pressed.

9. The defibrillator of claim 1, 4, or 5
    wherein the defibrillator further comprises a cover portion, and at least some of the graphics are provided on the cover portion of the defibrillator control box.

10. The defibrillator of claim 9
    wherein at least some of the graphics are provided on the outside of the cover portion of the defibrillator.

11. The defibrillator of claim 10 wherein the graphics on the cover portion include a picture indicating that the cover should be removed from the defibrillator.

12. The defibrillator of claim 10 wherein the cover portion includes a space provided for local emergency information.

13. The defibrillator of claim 12 wherein the cover portion includes a window behind which a card bearing local emergency information can be placed.

14. The defibrillator of claim 1, 4, or 5 wherein at least some of the graphics comprise backlit, translucent images.

15. The defibrillator of claim 1, 4, or 5 wherein the graphics include one or more pictures indicating that the caregiver should place a passive airway support under the shoulders of the patient.

* * * * *